United States Patent [19]

Kurtz

[11] Patent Number: 4,535,247
[45] Date of Patent: Aug. 13, 1985

[54] WATER STERILIZATION SYSTEM

[76] Inventor: Mark E. Kurtz, P.O. Box 1707, Rutland, Vt. 05701

[21] Appl. No.: 512,483

[22] Filed: Jul. 11, 1983

[51] Int. Cl.³ ............................................. G01N 21/00
[52] U.S. Cl. .................................. 250/436; 250/455.1
[58] Field of Search ...................... 250/455.1, 435, 436, 250/432

[56] References Cited

U.S. PATENT DOCUMENTS

| | | | |
|---|---|---|---|
| 1,051,350 | 1/1913 | Nogier | 422/24 |
| 1,486,473 | 3/1924 | Ailhaud | 422/24 |
| 3,562,520 | 2/1971 | Hippen | 250/43 |
| 4,141,686 | 2/1979 | Lewis | 250/436 |
| 4,189,363 | 2/1980 | Beitzel | 204/157.1 R |
| 4,255,663 | 3/1981 | Lewis | 250/436 |
| 4,320,085 | 3/1982 | Takeguchi et al. | 250/436 |

FOREIGN PATENT DOCUMENTS 674555 11/1963 Canada .
767856 9/1967 Canada .
1459395 12/1976 United Kingdom .

Primary Examiner—Bruce C. Anderson
Attorney, Agent, or Firm—Richard L. Hansen

[57] ABSTRACT

A water sterilization system includes a sterilizer having a plastic housing and a sheath inside the housing which transmits untraviolet light from an enclosed lamp. The housing is protected from uv degradation by means of a reflective liner. A fail-safe control mechanism is provided which includes a normally closed water valve held open by a stallable electric motor electrically in series with a photoresistor which senses the ultraviolet light.

18 Claims, 7 Drawing Figures

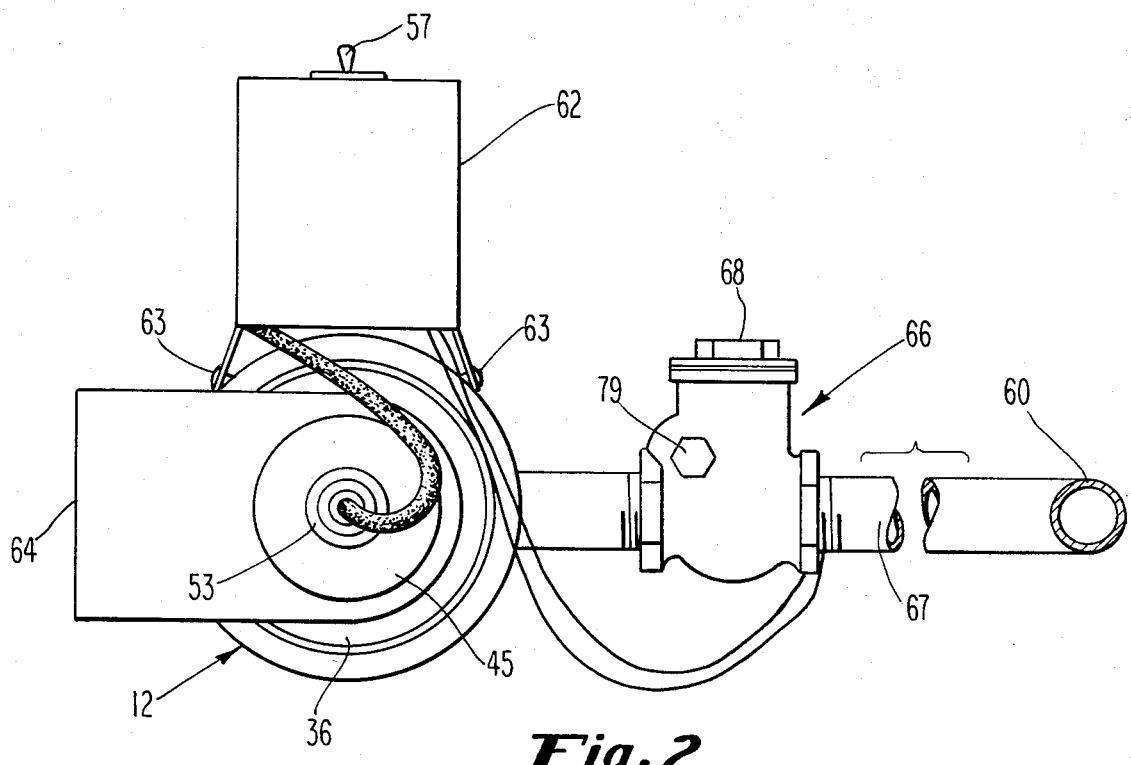
_Fig. 2_
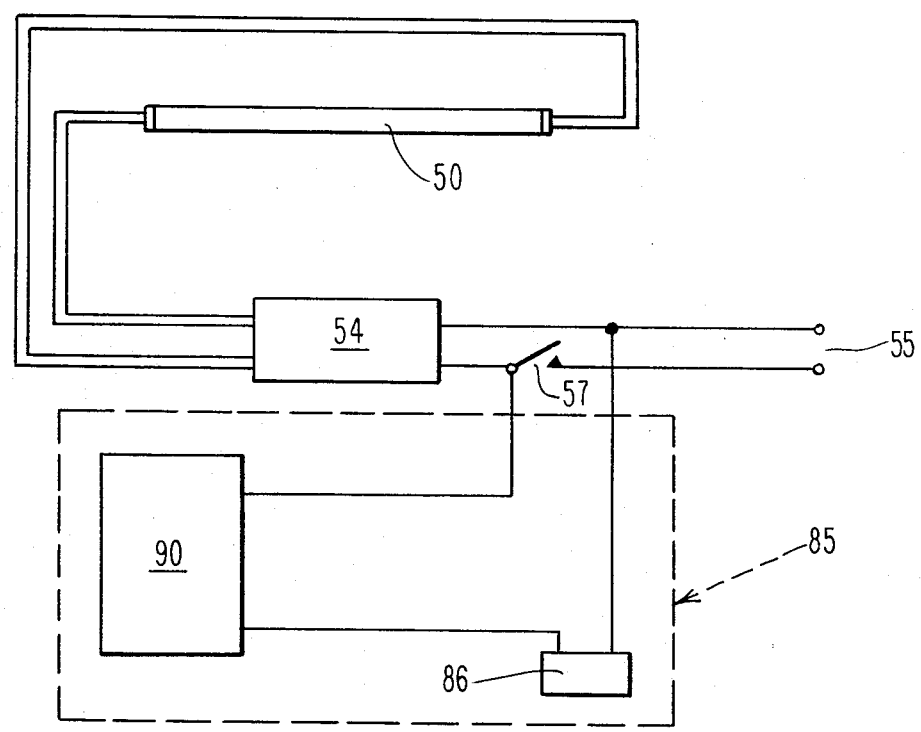
_Fig. 7_

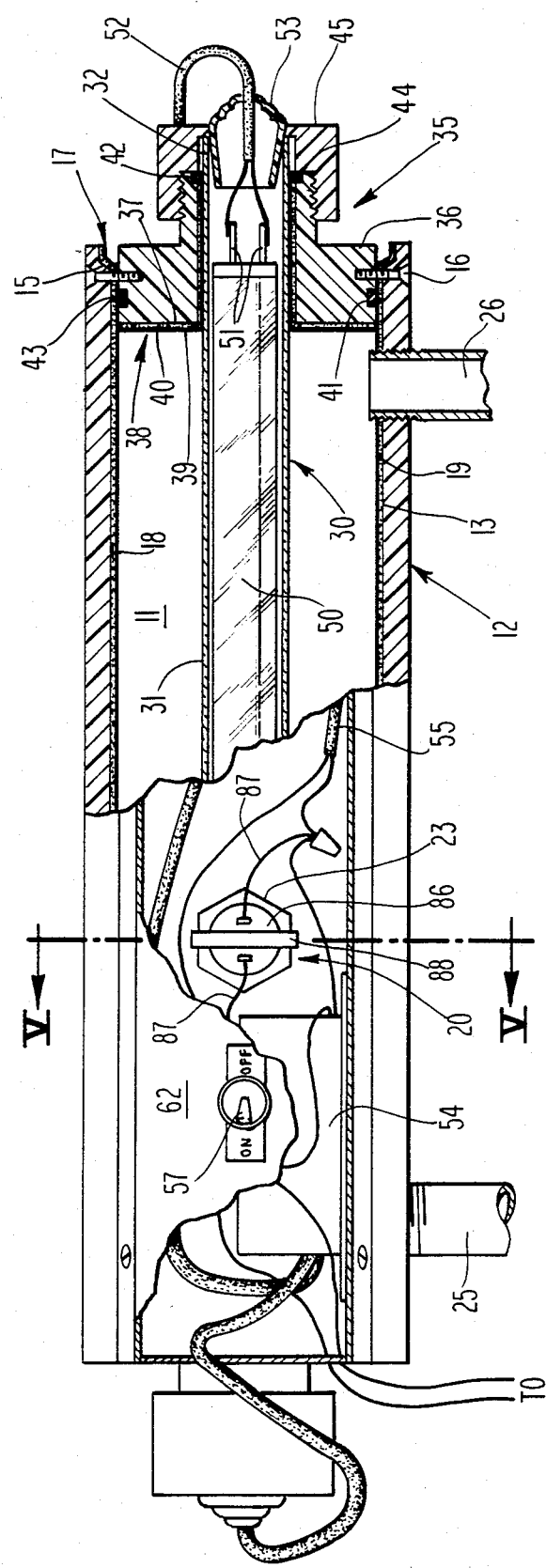

WATER STERILIZATION SYSTEM

This invention is in the field of water sterilization equipment; more specifically, apparatus which employs ultraviolet light to kill bacteria.

It is often not only desirable, but necessary, to purify water to be used for industrial and, especially, domestic or household purposes. It is known in the art of water purification that bacterial contamination can be killed by treating the water with chlorine, a process in common use by municipal water systems. It is also known that such bacteria can be rendered harmless by treating the water with ozone or irradiating the water with ultraviolet light. The useful UV wavelengths lie in the range of about 200–400 nm, and the intense radiation at about 254 nm from an electric mercury arc lamp is often used.

Sterilizers which employ UV light are especially attractive to individual domestic water users, not only those who have their own wells, but also urbanites who use municipal water and desire peace of mind. Such sterilizers are relatively easy to install and require little maintenance or attention. They are most conveniently adapted for connection to both a central incoming water line and a 110–120 volt AC power line. In addition, control mechanism is often provided to automatically shut off the water should the lamp fail.

The fail-safe mechanism in many sterilization systems disclosed in the early prior art included a solenoid-controlled water valve, the solenoid being connected in series with the UV lamp. In these mechanisms lamp failure opened the DC electrical circuit, allowing the close-biased water valve to shut; e.g., U.S. Pat. Nos. 1,051,350 and 1,486,473. The more recent systems employ AC power, and the fail-safe mechanisms are generally more complicated and expensive. They may include a rectifier if a solenoid-controlled valve is to be used; e.g., U.S. Pat. Nos. 4,141,686 and 4,255,663. Alternatively, indirect sensing, consisting of a photocell or electric eye, which is reactive to the light, can be used to activate a solenoid-controlled or magnetic water valve; e.g., U.S. Pat. No. 3,562,520 and Canadian Pat. Nos. 674,555 and 767,856.

One of the disadvantages of the water sterilization systems presently available is their high cost, which puts them beyond the reach of many who need them. The high cost is due in large measure to several construction features. Complicated fail-safe mechanisms were cited above. In addition, stainless steel has been the material of choice for the sterilizer housing, even though it is expensive and difficult to fabricate. Stainless steel is not adversely affected by continuous contact with water, it is easy to clean, it is not degraded by the ultraviolet light, and it does not itself add contaminants to the water. Plastic materials are now available from which sterilizers could be fabricated, and plastic housings can be employed. Indeed, the use of plastic so reduces the cost that plastic throw-away sterilizers have been suggested; e.g., U.S. Pat. Nos. 4,141,686 and 4,255,663.

If a plastic sterilizer is thrown away after a short period of use, the fact the plastic is severely affected by the ultraviolet radiation incident on it may not constitute a problem. However, if the sterilizer is not thrown away on schedule, UV-induced degradation of the plastic may lead to structural failure. Of equal concern to those who sterilize their water, the degradation can give rise to noxious degradation products which themselves contaminate the water. For example, PVC pipe is used in such sterilizers, and it is well known that the polyvinyl chloride plastic produces vinyl chloride, a suspected carcinogen, when irradiated with UV light. Furthermore, the light absorbed by the plastic housing does not kill bacteria and is wasted.

Thus, it is one object of this invention to provide a predominately plastic UV water sterilizer which is not degraded by the ultraviolet light, is suited for long-term use, and is inexpensively constructed for use in a UV water sterilization system. It is another object of this invention to provide a simple, inexpensive, line-operated fail-safe mechanism to shut the water off in the event of UV lamp failure. Other objectives will be evident to those skilled in the water sterilization art, to whom this specification is directed.

In attaining the aforesaid objectives, this invention provides a water sterilizer which includes (1) an elongated cylindrical housing of a plastic normally degraded by ultraviolet light, having opposing ends and an inside wall, said inside wall being covered with a protective liner to expose an ultraviolet light-reflecting inner surface; (2) a hollow, open-ended cylindrical sleeve of a material transmitting ultraviolet light, extending coaxially within said housing, and having an outer surface spaced from said inner surface to form an annular water chamber; (3) closure means affixed at each of said opposing ends for sealing said chamber; (4) water inlet and outlet conduits in communication with said chamber and adapted to connect to a central water supply; (5) a UV electric lamp enclosed within said sleeve, said lamp carrying terminals to receive electric power from leads fed into said sleeve; together with (6) a lamp power supply connected electrically to said lamp terminals and adapted to connect to an AC power line.

This invention also provides fail-safe control mechanism for use with a water stabilizer which utilizes an electric lamp emitting UV light, having water inlet and outlet conduits in communication with a water chamber and adapted to connect to a central water supply, which mechanism includes (1) a normally closed water valve in said inlet or outlet conduit; and (2) a series electrical circuit adapted to be AC line-powered and including (a) a photoresistor adapted to receive light from said lamp, the resistance of said photoresistor decreasing as the intensity of the light increases, and (b) a stallable electric motor coupled mechanically to said water valve to hold said valve open so long as said photoresistor receives sufficient light that an operating voltage appears across the motor.

Furthermore, this invention provides a complete water sterilization system which combines the aforesaid sterilizer and fail-safe control mechanism.

For a more complete understanding of the invention and the advantages associated with its use, attention is directed to the following description. The description should be read with reference to the drawings which are part of this application and illustrate a specific embodiment containing optional features.

In the drawings:

FIG. 2 is an end elevation view of the sterilization system of FIG. 1.

FIG. 4 is a cross-sectional view, with parts broken away, taken along line IV—IV in FIG. 3.

FIG. 5 is a vertical cross-sectional view taken along line V—V in FIG. 4.

FIG. 6 is a vertical cross-sectional view taken along line VI—VI in FIG. 1.

FIG. 7 is a schematic electrical circuit diagram for the water sterilization system of FIG. 1.

Figure 1:
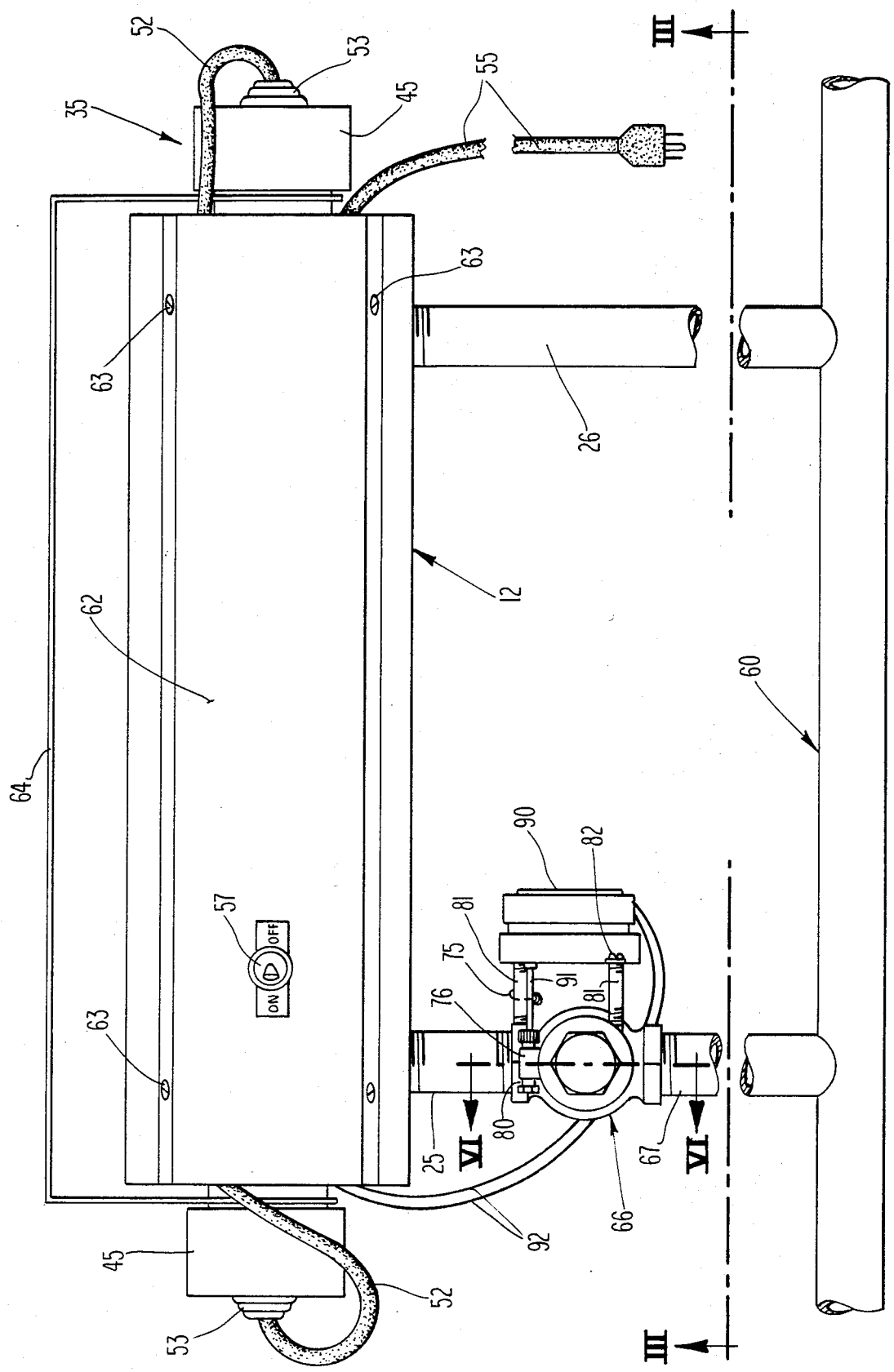
FIG. 1 is a plan view of a water sterilization system according to this invention.
Figure 3:
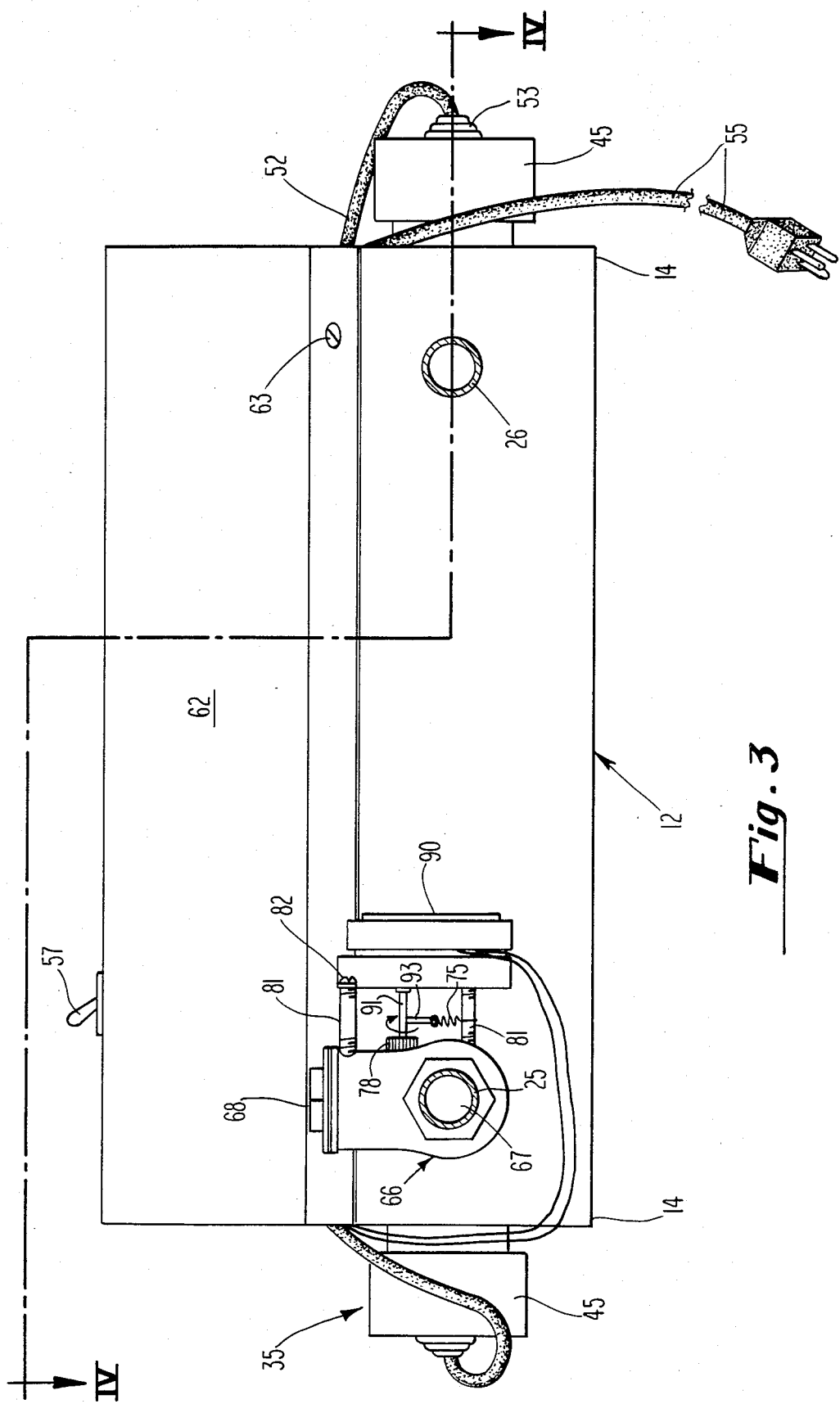
FIG. 3 is a front elevation view, partially in section, of the sterilization system taken along line III—III in FIG. 1.

Referring first to FIGS. 1–3, which illustrate the externally apparent features of the sterilization system, the sterilizer includes housing 12. The housing is cylindrical in shape, hollow and elongated. It is a feature of this invention that the housing is constructed of a plastic which is normally degraded by ultraviolet light. Such materials include almost all common filled or unfilled plastics, nearly all of which absorb UV light. For example, suitable plastics are polystyrene and copolymers thereof with acrylonitrile or butadiene, polyacrylates or methacrylates, polyurethanes, phenolic resins, polyvinyl compounds, and the like. Among the common plastics, filled polyvinyl chloride (PVC) pipe is readily available, inexpensive and especially useful.

Inside the housing, not seen in FIGS. 1–3, but described in detail below, is a pipe-like, cylindrical sleeve, which extends coaxially the length of the housing and encloses a UV electric lamp. The sleeve, together with the housing, define a ring-shaped water chamber. Opposing ends 14 of housing 12 carry end closure means 35, including gland nut 45, to seal the water chamber.

Housing 12 is penetrated by water inlet conduit 25 and water outlet conduit 26, both of which communicate with the water chamber and are adapted to connect with central water supply line 60 by means of standard soldered or threaded fittings. These conduits preferably are located in spaced apart relationship near the opposing ends of the housing.

Optional, but desirable, features include mounting bracket 64, which supports the sterilizer by engaging closure means 35 and can be attached to a wall or other fixed structure. Wiring cover 62 may be removably fastened to the housing with screws 63. Both the mounting bracket and wiring cover can be fabricated readily from sheet aluminum.

The wiring cover is separated from housing 12 at opposing ends 14, permitting passage of lamp electrical leads 52 and AC power cord 55. Rubber caps 53 are provided to close the ends of the sleeve. On/off electrical switch 57 is conveniently located on the wiring cover, but may be placed elsewhere as desired.

The internal structure of the sterilizer, which is substantially the same at both ends, is shown in FIGS. 4 and 5. Inside wall 13 of plastic housing 12 is covered by protective liner 17. Liner 17 has inner surface 18, chosen to reflect the UV light, thereby shielding housing 12 and returning the radiation to the interior. Liner 17 may be a thin, e.g., 3 mil, stainless steel sheet, aluminum foil, metalized polymeric film, e.g., polyester, or the like. Although the protective liner need not be fastened to the housing, it is often desirable to affix liner 17 to inside wall 13 of housing 12 with adhesive 19, and a silicone adhesive is generally satisfactory. As an alternative, a thin layer of reflective metal, such as aluminum, silver or gold, may be deposited directly on inside wall 13 by vapor or chemical deposition, thus producing protective liner 17.

Ultraviolet lamp 50, enclosed within sleeve 30, carries terminals 51 to receive electric power from leads 52 fed into ends 32 of the sleeve from lamp power supply 54. Power supply 54 is in turn adapted, through switch 57, to connect to an AC power line through electrical cord 55. In this regard, attention is directed to FIG. 7. The UV lamp may be a germicidal lamp of the type available from General Electric Co., for example. The sleeve must transmit into annular water chamber 11 at least some of the ultraviolet light emitted by the lamp.

Water chamber 11 is created by spacing sleeve outer surface 31 from inner surface 18 of protective liner 17. A limited number of materials are suitable for sleeve 30; quartz and fused silica are relatively transparent to UV light and may be employed.

Although it is necessary to seal the opposing ends of housing 12, the details of the end closure are not critical, and suitable closures are described in prior art such as U.S. Pat. No. 4,255,663 and Canadian Pat. No. 674,555. A preferred end closure is shown in the drawings.

End closure 35, which is used at both ends of housing 12, may be made predominately of plastic, such as those listed above. The end closure includes circular insert plug 36 and gland nut 45. Plug 36 is grooved circumferentially to provide seat 41 for inner O ring 43. The plug is sized to fit snugly when pressed into the end of the housing, a water-tight seal between the plug and inner surface 18 being provided by O ring 43. The plug is secured in place with screws 16. Chamfer 15 is advantageously cut around the end of housing 12 to facilitate entrance of the plug.

Plug 36 is axially bored to receive sleeve 30, which extends beyond the end of the housing in this closure. The outer end of plug 36 is counterbored to provide O ring seat 42 and is provided with external threads to be engaged by corresponding inner threads in gland nut 45. When the gland nut is tightened down, compression of O ring 44 provides a water-tight seal between the plug and outer surface 31 of sleeve 30.

Inside surface 37 of insert plug 36 is optionally provided with protective cover 38. Protective cover 38, like protective liner 17, has a UV reflective interior surface 39. Cover 37 may, but need not, be constructed of the same material as liner 17, and materials from those recited above may be used. Cover 38 may be affixed to inside surface 37 with adhesive 40.

The sterilizer may optionally also have associated with it means to monitor the status of ultraviolet lamp 50. For example, the electrical circuit containing the lamp may be equipped with a warning buzzer or light, and a light emitting diode (LED) may be employed to signal that the lamp is operating. As an alternative, housing 12 may be drilled and tapped to accommodate viewing port 20, which is shown in FIGS. 4 and 5. The viewing port includes threaded nipple 22, window 21 and retainer nut 23. The window may be glass, quartz or fused silica, depending upon its function. Any of the fail-safe control mechanisms disclosed in the prior art which utilize such a viewing port may be used with the sterilizer of this invention.

However, it is preferred that the fail-safe control mechanism described hereinafter be employed with the sterilizer of this invention. The fail-safe control mechanism includes a normally closed water valve in either the water inlet or outlet conduit. A normally closed water valve is biased to remain shut and prevent the passage of water therethrough unless a counterforce is applied which overcomes the bias and opens the valve. Several types of normally closed water valve are suitable for use in this invention, e.g., poppet, ball check, ball, diaphragm, plug, and swing check valves, means being provided to hold them open. Among these valve types, swing check valve 66, shown in FIGS. 1–3 and 6, is very satisfactory.

Referring first to FIG. 6, swing check valve 66 is oriented in the water line so the water enters at inlet 67 and leaves at exit 72. Circular valve member 70 rotates about shaft 91 with respect to circular valve seat 69; set screw 73, accessible through inspection port 68, couples the valve member to the shaft. Then the valve member is seated, rubber gasket 74 engages seat 69, the valve is closed, and water is prevented from flowing through inlet 67 to exit 72. It is evident that water pressure alone will tend to keep the valve closed, and return spring 75 reinforces that tendency. Outlet 72 of the valve leads to inlet conduit 25 of the sterilizer. It should be noted, however, that the valve could as well be used with sterilizer outlet conduit 26 led into valve inlet 67.

As most clearly shown in FIGS. 1–3, shaft 91, to which valve member 70 is coupled, is carried for rotation in shaftway 76, which is sealed at one end with washer 80 held by seal bolt 79. Shaft 91 emerges from the other end of the shaftway, which is sealed with packing nut 78. Shaft 91 carries perpendicular spring arm 93, to which one end of return spring 75 is connected. The other end of return spring 75 is connected to motor standoff 81. The direction of counterforced shaft rotation is indicated in FIG. 3; return spring 75 opposes the counterforced rotation of the shaft and tends to bias the valve closed. The length of spring arm 93 and the size of return spring 75 will be selected to ensure the valve closes if the ultraviolet light fails.

The fail-safe control mechanism of this invention also includes series electrical circuit 85 (see FIG. 7) adapted to be AC line powered. The electrical circuit utilizes photoresistor 86 to sense the ultraviolet lamp operation and stallable electric motor 90 to provide the counterforce to keep the valve open.

Stallable electric motor 90 is coupled to one end of shaft 91 and is intended to run continuously, rotating shaft 91 in the direction shown by the arrow in FIG. 3, thereby overcoming the bias provided by return spring 75 and the water pressure and holding water valve 66 open. The internal clearances in the valve preclude complete rotation of valve member 70, so motor 90 will stall. Thus, it is a requirement of this invention that motor 90 be capable of running in a stalled condition for an indefinite, but prolonged, period of time. Although, with proper cooling, several types of motors can satisfy this requirement, cooling is generally inconvenient and adds to the cost. Thus, it is preferred that the stallable motor be a synchronous motor of the hysteresis or reluctance types. Such motors are commercially available; e.g., they can be obtained from Hansen Manufacturing Co. in Princeton, Ind. The motor will run and keep the water valve open so long as an operating voltage appears across it.

The voltage that appears across the motor is determined in part by the electrical impedance of photoresistor 86. In series circuit 85 the 110–120 v line voltage is apportioned across motor 90 and photoresistor 86 in direct proportion to their impedances. Only if the impedance of the photoresistor is very low compared with the input impedance of the motor will an operating voltage appear across the motor. Thus, it is the impedence of photoresistor 86 which determines whether motor 90 runs, whether valve 66 is open, and whether water flows through the sterilizer. When the impedance of the photoresistor is driven by light from the sterilizer, the circuit functions as a fail-safe control mechanism in the water sterilization system.

Photoresistor 86, equipped with electrical leads 87, is adapted by any suitable means to receive light from ultraviolet lamp 50, and this is conveniently accomplished by providing a recess in retainer nut 23 to hold the photoresistor in proximity to viewing port 20. Holddown strap 88 retains the photoresistor in position. In principle, any electrical resistor which will function under an applied potential of 110–120 vac and whose resistance will change sufficiently with radiation from the ultraviolet lamp is satisfactory. Specific examples of such photoresistors are cadmium sulfide and cadmium selenide photo cells, which respond in the wavelength range about 400–800 nm. Suitable photocells are available from Silonex Co. in Montreal, Canada.

It will be evident that the suitability of a given set of components to control a particular water valve will depend upon the characteristics of the system, but selection of appropriate components is not difficult in view of the principles set forth above. As a specific, but non-limiting example, a swing check valve in a ¾ inch water line was controlled with a 110–120 v electrical circuit which included a 5 watt hysteresis motor, supplying a drive torque of 7 in.-oz., and geared to 6 rpm obtained from Hansen Manufacturing Co. The motor was in series with a Mod NSL 495 cadmium sulfide photoconductive cell obtained from Silonex Co. This cell can carry 60 ma, has a resistance in the dark of 32 megaohms and 1 megaohm when irradiated with visible light at an intensity of 100 ft-candles.

It will be appreciated that a number of variations in the details of the invention can be made while remaining within the scope of the following claims.

What is claimed is:

1. A water sterilization system which includes a sterilizer comprising an elongated cylindrical housing of a plastic normally degraded by ultraviolet light, having opposing ends and an inside wall, said inside wall being covered with a protective liner to expose an ultraviolet light-reflecting inner surface; a hollow, open-ended cylindrical sleeve of a material transmitting ultraviolet light, extending coaxially within said housing, and having an outer surface spaced from said inner surface to form an annular water chamber; closure means affixed at each of said opposing ends for sealing said chamber, including a plastic insert plug having an inside surface lined with a protective cover to expose an ultraviolet light-reflecting interior surface; water inlet and outlet conduits in communication with said chamber and adapted to connect to a central water supply; a UV electric lamp enclosed within said sleeve, said lamp carrying terminals to receive electric power from leads fed into said sleeve; together with a lamp power supply connected electrically to said lamp terminals and adapted to connect to an AC power line; in combination with fail safe control mechanism comprising a normally closed water valve in said inlet or outlet conduit; and a series electrical circuit adapted to be AC line-powered and including a photoresistor adapted to receive light from said lamp, the resistance of said photoresistor decreasing as the intensity of the light increases, and a stallable electric motor coupled mechanically to said water valve to hold said valve open so long as said photoresistor receives sufficient light than an operating voltage appears across said motor;

whereby UV-induced degradation of the plastic wetted surfaces and contamination of the water by the degradation products are avoided.

2. The system of claim 1 wherein said housing is constructed of polyvinyl chloride plastic.

3. The system of claim 1 wherein said protective liner is affixed to said inside wall by means of an adhesive.

4. The system of claim 1 wherein said protective liner is stainless steel sheet.

5. The system of claim 1 wherein said insert plug has O rings to seal said plug to said housing and said sleeve.

6. The system of claim 1 further comprising a viewing port which transmits light from said lamp through said housing.

7. The system of claim 1 wherein said normally closed water valve is a swing check valve.

8. The system of claim 1 wherein said photoresistor is a line-operated cadmium sulfide photocell.

9. The system of claim 1 wherein said stallable electric motor is a hysteresis motor.

10. A water sterilizer which comprises an elongated cylindrical housing of a plastic normally degraded by ultraviolet light, having opposing ends and an inside wall, said inside wall being covered with a protective liner to expose an ultraviolet light-reflecting inner surface;

a hollow, open-ended cylindrical sleeve of a material transmitting ultraviolet light, extending coaxially within said housing, and having an outer surface spaced from said inner surface to form an annular water chamber;

closure means affixed at each of said opposing ends for sealing said chamber, including a plastic insert plug having an inside surface lined with a protective cover to expose an ultraviolet light-reflecting interior surface;

water inlet and outlet conduits in communication with said chamber and adapted to connect to a central water supply;

a UV electric lamp enclosed within said sleeve, said lamp carrying terminals to receive electric power from leads fed into said sleeve; together with a lamp power supply connected electrically to said lamp terminals and adapted to connect to an AC power line;

whereby UV-induced degradation of the plastic wetted surfaces and contamination of the water by the degradation products are avoided.

11. The sterilizer of claim 10 wherein said housing is constructed of polyvinyl chloride plastic.

12. The sterilizer of claim 10 wherein said protective liner is affixed to said inside wall by means of an adhesive.

13. The sterilizer of claim 10 wherein said insert plug has O rings to seal said plug to said housing and said sleeve.

14. The sterilizer of claim 10 wherein said protective liner and said protective cover are both stainless steel sheet.

15. Water sterilizer apparatus which comprises a water chamber;

an electric lamp emitting UV light within said chamber;

water inlet and outlet conduits in communication with said water chamber and adapted to connect to a central water supply;

a normally closed water valve in said inlet or outlet conduit; together with series electrical circuit fail-safe control mechanism adapted to be AC line-operated and consisting of a photoresistor adapted to receive light from said lamp, the resistance of said photoresistor decreasing as the intensity of the light increases, and a stallable electric motor coupled mechanically to said water valve to hold said valve open so long as said photoresistor receives sufficient light that an operating voltage appears across said motor.

16. The apparatus of claim 15 wherein said normally closed water valve is a swing check valve.

17. The apparatus of claim 15 wherein said photoresistor is a line-operated cadmium sulfide photocell.

18. The apparatus of claim 15 wherein said stallable electric motor is a hysteresis motor.

* * * * *